United States Patent [19]
Davidson et al.

[11] Patent Number: 5,628,790
[45] Date of Patent: May 13, 1997

[54] ZIRCONIUM OXIDE ZIRCONIUM NITRIDE COATED VALVULAR ANNULOPLASTY RINGS

[75] Inventors: James A. Davidson, Collierville, Tenn.; Kenneth P. Daigle, Olive Branch, Miss.

[73] Assignee: Smith & Nephew, Inc., Memphis, Tenn.

[21] Appl. No.: 547,127

[22] Filed: Oct. 24, 1995

Related U.S. Application Data

[63] Continuation-in-part of Ser. No. 112,587, Aug. 26, 1993, Pat. No. 5,496,359, which is a continuation-in-part of Ser. No. 919,932, Jul. 27, 1992, Pat. No. 5,282,850, which is a continuation-in-part of Ser. No. 830,720, Feb. 4, 1992, Pat. No. 5,258,022, which is a continuation-in-part of Ser. No. 557,173, Jul. 23, 1990, Pat. No. 5,152,794, which is a continuation-in-part of Ser. No. 385,285, Jul. 25, 1989, Pat. No. 5,037,438.

[51] Int. Cl.$^6$ .................................................. A61F 2/24
[52] U.S. Cl. ...................... 623/2; 623/1; 623/3; 623/11; 623/66
[58] Field of Search .................. 623/1, 2, 3, 11, 623/66

[56] References Cited

U.S. PATENT DOCUMENTS

| | | |
|---|---|---|
| 2,987,352 | 6/1961 | Watson et al. . |
| 3,643,658 | 2/1972 | Steinemenan . |
| 3,677,795 | 7/1972 | Bokros et al. . |
| 3,685,059 | 8/1972 | Bokros et al. .................. 623/2 |
| 3,969,130 | 7/1976 | Bokros ............................ 623/2 |
| 4,040,129 | 8/1977 | Steinemann et al. . |
| 4,145,764 | 3/1979 | Suzuki et al. . |
| 4,159,358 | 6/1979 | Hench et al. . |
| 4,223,412 | 9/1980 | Aoyagi et al. . |
| 4,495,664 | 1/1985 | Blanquaert . |
| 4,608,051 | 8/1986 | Reck et al. . |
| 4,617,024 | 10/1986 | Broemer et al. . |
| 4,652,459 | 3/1987 | Engelhardt . |
| 4,652,534 | 3/1987 | Kasuga . |
| 4,671,824 | 6/1987 | Haygarth ....................... 148/6.11 |
| 4,687,487 | 8/1987 | Hintermann . |
| 4,714,474 | 12/1987 | Brooks, Jr. et al. . |
| 4,728,488 | 3/1988 | Gillett et al. . |

(List continued on next page.)

FOREIGN PATENT DOCUMENTS

| | | |
|---|---|---|
| 770080 | 10/1967 | Canada . |
| 1140215 | 1/1983 | Canada . |
| 0410711A1 | 7/1990 | European Pat. Off. . |
| 2811603 | 3/1978 | Germany . |
| 08939 | 4/1986 | Japan . |
| 180679 | 7/1986 | Japan . |
| 1325269 | 8/1973 | United Kingdom . |
| 2206182 | 5/1987 | United Kingdom . |
| 2206182 | 12/1988 | United Kingdom . |

OTHER PUBLICATIONS

O'Connor, Leo, "Novacor's VAD: How to Mend a Broken Heart," Mechanical Engineering, Nov. 1991 pp. 53–55.
Korane, Kenneth, "Replacing the Human Heart," Machine Design, Nov. 7, 1991, pp. 100–105.

(List continued on next page.)

*Primary Examiner*—John G. Weiss
*Assistant Examiner*—Francis K. Cuddihy
*Attorney, Agent, or Firm*—Pravel, Hewitt, Kimball & Krieger

[57] ABSTRACT

An annuloplasty ring fabricated from a component of a low elastic modulus metal coated with blue to black zirconium oxide or yellow to orange zirconium nitride. The coating provides enhanced thrombogenicity, biocompatibility, hemocompatibility, corrosion-resistance, friction and microfretting resistance, durability, and electrical insulation. The coatings can be applied to the underlying low modulus metallic components by physical or chemical vapor deposition as well as other ion-beam assisted methods. Preferably, however, for optimizing attachment strength, the annuloplasty ring components are fabricated from zirconium or zirconium-containing alloys and the coatings are formed by oxidizing or nitriding through an in situ method.

13 Claims, 3 Drawing Sheets

U.S. PATENT DOCUMENTS

| | | | |
|---|---|---|---|
| 4,778,461 | 10/1988 | Pietsch et al. | 623/2 |
| 4,822,355 | 4/1989 | Bhuvaneshwar | 623/2 |
| 4,834,756 | 5/1989 | Kenna . | |
| 4,955,911 | 9/1990 | Frey et al. . | |
| 5,037,438 | 8/1991 | Davidson . | |
| 5,061,278 | 10/1991 | Bicer . | |
| 5,229,162 | 7/1993 | Chapman et al. | 623/1 |

OTHER PUBLICATIONS

Baruah Bileaflet Mechanical Cardioc Valve Prosthesis, "Instructions for Use" brochure (Author and date unknown).

Pamphlet, "Zircadyne Corrosion Properties," Teledyne Wah Change Albany (no date) pp.1–16.

Conte, Borello, and Cabrini, "Anodic Oxidation of Zircaloy-2," Journal of Applied Electrochemistry, vol. 6, pp. 293–299 (1976).

Budinski, K.G., "Tribological Properties of Titanium Alloys," vol. 1, *Wear of Materials*, AMSE (1991) pp. 289–299.

Bill, R.C., "Selected Fretting–Wear–Resistant Coatings for Ti–6%Al–%Allo Wear" 106 (1985), pp. 283–301.

Bertrand, G., et al., "Morphology of Oxyde Scales Formed on Titanium," vol. 21, *Oxidation of Metals*, Nos. 1/2 (1983), pp. 1–19.

More, R.B., Silver, M.D., "Pyrolytic Carbon Prosthetic Heart Valve Occluder Wear: In Vivo vs. In Vitro Results for the Bjork–Shiley Prosthesis," *Journal of Applied Biomaterials*, vol. 1, pp. 267–278 (1990).

Kowbel, W., et al., "Effect of Boron Ion Implantation on Tribological Properties of CVD $Si_3N_4$," vol. 46, *Lubrication Engineering*, 10 pp. 645–650.

Author Unknown, "Boric Acid: A self–replenishing solid lubricant," Tex Spotlight, Advanced Materials and Processes, pp. 40–42 (Jul. 1991).

"Increase in Biocompatibility of Polymers by Treatment with Phosphatidyl Choline," Study done by Biocompatibles, Ltd., U.K. and Wolfson Centre for Materials Technology Brunel University (Jul. 1991).

Golomb, G., et al., "Prevention of bioprosthetic heart valve tissue calcification by charge modification: Effects of protamine binding by formaldehyde," vol. 25, *J. of Biomedical Materials Research*, pp. 85–98 (1991).

Akins, Cary W., "Mechanical Cardiac Valvular Prostheses," Current Review by the Society of Thoracic Surgeons, pp. 161–172 (1991).

Haygarth and Fenwick, "Improved Wear Resistance of Zirconium by Enhanced Oxide Films," Thin Solid Films, Metallurgical, and Protective Coatings, vol. 118, pp. 351–362 (1984).

"The Cementless Fixation of Hip Endoprosthesis," edited by Morscher, Mittelmeier, 'Total Hip Replacement with the Autophor Cement–Free Ceramic Prosthesis,' pp. 225–241 (1984).

Brown and Merritt, "Evaluation of Corrosion Resistance of Bioloy," Dept. of Biomedical Engineering, Case Western Reserve University, Feb. 13, 1986 (1:8).

Davidson, et al., "Wear, Creep and Frictional Heating of Femoral Implant Articulating Surfaces and the Effect on Long–Term Performance —Part II, Friction, Heating, and Torque," *J. of Biomedical Materials Research: Applied Biomaterials*, vol. 22, No. A1, pp.

ASTM F86–84, "Standard Practice for Surface Preparation and Marking of Metallic Surgical Implants," pp. 12–14 (1984), corrected editorially in May 1987.

Khruschov, "Principles of Abrasive Wear," Wear 28, 69–88 (1974).

Weightman and Light, "The Effect of the Surface Finish of Alumina and Stainless Steel on the Wear Rate of UHMW Polyethylene," *Biomaterials*, 7, 20–24 (1986).

Viegas, et al., "Metal Materials Biodegration: A Chronoamperometric Study," *J. of Materials Science: Materials in Medicine*, 1, 105–109 (1990).

Briscoe, et al., "The Friction and Wear of High Density Polythene: The Action of Lead Oxide and Copper Oxide Fillers," *Wear* 27, 19–34 (1974).

Rabinowicz, "Lubrication of Metal Surface by Oxide Films," ASLE Translations, 10, 400–407 (1967).

Mausli, et al., "Constitution of Oxides on Titanium Alloys for Surgical Implants," *Advances in Bio Materials*, 8, p. 305 (1988).

Rokicki, "The Passive Oxide Film on Electropolished Titanium" (Feb. 1990).

Coll and Jacouot, "Surface Modification of Medical Implants and Surgical Devices Using TiN Layers," *Surface and Coatings Technology*, 36, p. 867 (1988).

Bradhurst and Heuer, "The Influence of Oxide Stress on the Breakaway Oxidation of Zircaloy-2," *J. of Nuclear Materials*, 37, p. 35 (1970).

Demizu, et al., "Dry Friction of Oxide Ceramics Against Metals: The Effect of Humidity," *Tribology Transactions*, 33, p. 505 (1990).

ZIRCONIUM OXIDE ZIRCONIUM NITRIDE COATED VALVULAR ANNULOPLASTY RINGS

RELATED APPLICATION

This application is a continuation-in-part of U.S. Ser. No. 08/112,587 filed Aug. 26, 1993, issued as U.S. Pat. No. 5,496,359 on Mar. 5, 1996 which is in turn a continuation-in-part of U.S. Ser. No. 07/919,932, filed Jul. 27, 1992, issued as U.S. Pat. No. 5,282,850 on Feb. 1, 1996 which is in turn a continuation-in-part of U.S. Ser. No. 07/830,720 filed Feb. 4, 1992, issued as U.S. Pat. No. 5,258,022 on Nov. 2, 1993 which is in turn a continuation-in-part of U.S. Ser. No. 07/557,173, filed Jul. 23, 1990 and now U.S. Pat. No. 5,152,794 issued on Oct. 6, 1992, which is in turn a continuation-in-part of U.S. Ser. No. 07/385,285, filed Jul. 25, 1989, issued as U.S. Pat. No. 5,037,438 on Aug. 6, 1991.

BACKGROUND OF THE INVENTION

1. Field of the Invention

The present invention relates to valvular annuloplasty rings with enhanced biocompatibility and corrosion resistance. In particular, the invention relates to valvular annuloplasty rings constructed of zirconium oxide and zirconium nitride coated, low elastic modulus, metallic compositions.

2. Description of the Related Art

Valvular annuloplasty is a procedure for correcting deformities of the natural valves of the heart through implantation of a prosthesis, typically ring-shaped, which restores the shape of the deformed valve. Valvular annuloplasty is often utilized for correcting the tricuspid or mitral valves, although it is not restricted to those valves. Surgical alternatives to annuloplasty include replacement of the heart valve with a biological tissue valve or a mechanical valve.

Typical current annuloplasty rings are formed of a solid core, constructed from either a polymeric or metallic substance, with a woven polymeric sleeve or sheath, encasing the core. For example, U.S. Pat. No. 3,656,185 to Carpentier describes a ring core of stainless steel with a stitchable cord of polytetraflourethylene, both encased in a textile sheath, and U.S. Pat. No. 4,055,861 to Carpentier et al. describes an annuloplasty ring core constructed of a flexible biocompatible material enclosed in a textile sheath. U.S. Pat. No. 5,104,407 to Lam et al. describes a ring core made of a biocompatible material that is also antimagnetic, such as a cobalt-nickel alloy, with a knit polymeric outer sheath.

As with any surgical procedure, valvular annuloplasty faces complications that include malfunction of the ring due to distortion of the implant, physical or chemical deterioration of ring components, and tearing of the typical cloth sheath. The biocompatibility and physical characteristics (such as elasticity, strength, and wear resistance) of materials used in the annuloplasty ring components can be a factor in some of these complications.

Additionally, polymeric materials used in valvular annuloplasty constructs can degrade with time in the body. Water absorption and oxidation of the polymeric material can also adversely affect the material's properties, which can in turn lead to physical and structural alteration of the annuloplasty ring and adverse biological responses.

Metallic rings can experience damage of natural passive surface oxides via local movement of tissue or the sewing sheath. This local movement can produce metal ions, debris, and micro-electric currents which can adversely alter protein, tissue, platelet, and other cell attachments to the ring.

In an annuloplasty ring where the core is fabricated from a metallic element and the sewing ring or sheath is a polymer, there exists the possibility of metal ion release and micro-electrical (galvanic related) circuits due to abrasion between the polymeric sheath (also referred to as a sleeve) and metal core. The effect of metal ions and micro-electrical circuits on a biological environment is not entirely understood but it has been linked to adverse cellular, platelet, and protein response and the need for implant replacement.

Still needed in the art is a valvular annuloplasty ring construct with enhanced biocompatibility and elastic flexibility, having wear resistant surfaces with a subsequent reduction in metal ion release and reduced potential to create micro-electrical circuits.

SUMMARY OF THE INVENTION

The present invention provides annuloplasty rings fabricated from a low elastic modulus metallic composition, such as zirconium and zirconium-containing alloys, covered with a biocompatible, microfretting and corrosion-resistant, electrically insulative coating of blue to black zirconium oxide or yellow to orange zirconium nitride. These coatings are tightly adherent to the underlying metal and are of sufficient thickness to provide the desired physical characteristics.

BRIEF DESCRIPTION OF THE DRAWINGS

A better understanding of the present invention can be obtained when the detailed description of the preferred embodiments is considered in conjunction with the following drawings, in which.

DETAILED DESCRIPTION OF PREFERRED EMBODIMENT

Figure 1:
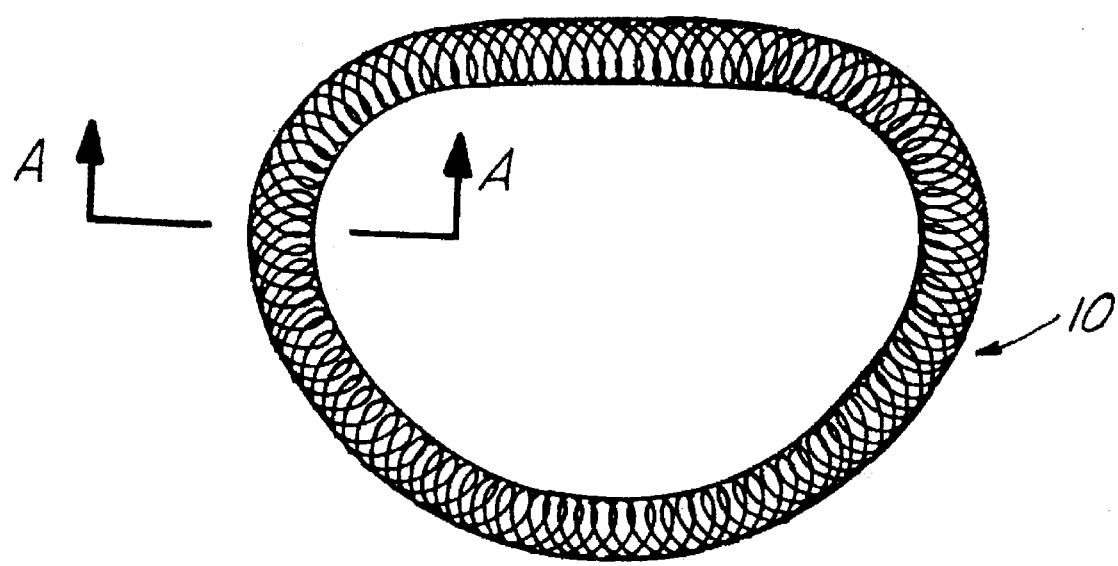
FIG. 1 is a schematic representation of an annuloplasty ring, which is commercially available under the trademark (CARPENTIER-EDWARDS PHYSIO) from Baxter Healthcare, Irvine, Calif.

The invention provides a low modulus metallic valvular annuloplasty ring prosthesis where at least one of its components is at least partially coated with a layer of ceramic blue to black zirconium oxide or zirconium nitride. These compounds provide a blood compatible, microfretting resistant, electrically insulative, stable and corrosion resistant ceramic coating. Furthermore, these coatings can be overlaid with a thin coating of phosphatidyl choline, heparin, or other surface treatments for further reducing platelet adhesion, if the annuloplasty ring will be in contact with blood. Other medicaments can also be coated onto the ceramic surfaces of the present invention. The ceramic coatings of the invention can also be modified by boronation or silver doping to further improve friction and wear characteristics.

The term "low modulus" as used to describe the preferred metallic compositions in this invention includes those metallic compositions that have a modulus of elasticity less than about 130 GPa.

The term "blue to black" as used to describe zirconium oxide means that the color of the oxide coatings may range from blue to black, depending on zirconium concentration in the underlying component metal, process conditions that produce the coating, or crystal structures of the coating. If pure zirconium is used, the blue to black zirconium oxide coating formed by the preferred in situ process has a substantially monoclinic structure. However, if a zirconium alloy is used, the in situ process will produce a surface containing a mixture of oxides with zirconium oxide being predominant. This will yield the blue to black appearance. If an ion beam deposition assisted process or other non-in situ process is used, such as chemical or vapor deposition, then the color of the deposited oxide is not affected by zirconium concentration in the underlying metallic composition. In this situation, a white tetragonal or a cubic structure is possible, as well as a structure that yields a blue to black coating. Coatings produced by non-in situ processes are useful as "overlay" coatings on an in situ blue-black zirconium oxide or yellow-orange zirconium nitride coating. Since the hardness levels of such overlays and the in situ coatings are more closely matched than the match between the hardness levels of overlay and component metal, the overlay coatings are more firmly attached to the in situ coatings and have superior integrity. Other hard coatings that can be used as overlays are amorphous diamond-like carbon coatings, wear-resistant coatings formed by silver deposition, and lubricious boronated coatings.

The term "yellow to orange," as applied to zirconium nitride, refers to the range of colors possible for the zirconium nitride coatings. The aforementioned comments about alloys and consequent mixtures of oxides with zirconium oxide also apply in the nitride context.

The thickness of the inventive hard zirconium oxide or nitride coating is preferably in a range from about 3 to about 6 microns for optimal residual compressive stresses and minimal dimensional changes or distortion during oxidation or nitridation. However, the thickness of the coating is frequently not critical, such as where the surface coating merely provides enhanced hemocompatibility and biocompatibility and is not subject to forces requiring optimal residual compressive stresses. Thus, in these situations, the thickness of the coating is limited only by its own integrity, such that it is not subject to cracking and spalling, thereby potentially releasing particulates into the body of the patient. These coatings can range from about 0.1 to about 20 microns or more in thickness.

While the oxide and nitride coatings of the invention can be applied by various coating methods, in situ coating is preferred. These in situ methods require that the metal composition be zirconium or a zirconium alloy so that the coating can be formed by oxidizing or nitriding the metal itself, not simply by depositing zirconium oxide or nitride on the metallic surface. Thus, the in situ methods include oxidation or nitridation in air, oxidation in oxygen, nitridation in nitrogen, and salt baths. These methods are described below.

In order to form continuous zirconium oxide or nitride coatings over the surface of zirconium alloys by an in situ method, the alloy should contain a range of about 50 to about 100 wt. % zirconium, preferably from about 80 to about 100 wt. %. Common alloying elements include niobium, tantalum, titanium and hafnium. Yttrium can also be alloyed with the zirconium to enhance the formation of a tougher, yttria-stabilized zirconium oxide coating during the oxidation of the alloy. During oxidation, the protective surface layer will contain various amounts of zirconium oxide depending on the alloy composition. The greater the level of zirconium oxide, the darker (tending to black) the ceramic oxide appearance. However, this appearance may be blue for alloys with relatively lower levels of zirconium or for thinner oxide layers. A monoclinic structured zirconium oxide surface is stable at room temperature and black in appearance. However, oxide structures such as cubic or tetragonal can range from grey to white in appearance. While zirconium and zirconium alloys can be custom-formulated by conventional methods known in the art of metallurgy, a number of suitable alloys are commercially available. These commercially available alloys include, for example, those sold under the trademarks (ZIRCADYNE 705), (ZIRCADYNE 702), and (ZIRCALLOY), and Ti-Zr and Ti-Mo-Zr alloys. Ti-Nb-Zr alloys are disclosed in U.S. Pat. No. 5,169,597 to Davidson et al., which is hereby fully incorporated by reference, and are the preferred low modulus metals. It should be understood that other low modulus metallic compositions not containing zirconium can also be used if the coating is applied by other than in situ methods, such as chemical vapor deposition and physical vapor deposition.

To coat an implant component with a corrosion-resistant, biocompatible, hemocompatible, durable, stable coating by an in situ process, the appropriate component is first produced and then subjected to processes which cause the natural (in situ) formation of a tightly adhered essentially zirconium oxide coating on its surface. The processes include, for example, oxygen-containing gas, steam, or water oxidation or oxidation in a fluidized or salt bath. These processes ideally provide a dense, blue to black, hard, durable, low-friction, wear-resistant, corrosion-resistant zirconium oxide film or coating of thicknesses typically less than several microns ($10^{-6}$ meters) on the surface of the component. In some instances, the zirconium-containing oxide coating can be as thin as 0.1–0.2 microns and still provide useful protection. Typically, below this zirconium-containing oxide coating, there is a zone where diffused oxygen from the oxidation process increases the hardness and strength of the underlying component metal, and optimizes coating durability and attachment strength. Thus, the fatigue strength of the underlying component metal is improved, thereby increasing the potential life of the prosthesis. In contrast, oxidation of titanium alloys as described in, for example, the aforementioned Steinemann patent, tends to form multiple oxides of titanium. These titanium oxides are less well attached to the underlying metal, and more importantly, stabilize the lower strength α-phase which significantly reduces the metal's fatigue strength.

The air, oxygen, steam, and water oxidation processes are described in now-expired U.S. Pat. No. 2,987,352 to Watson, the teachings of which are incorporated by reference as though fully set forth. The air oxidation process provides a firmly adherent black, blue-black, or blue layer of essentially zirconium oxide ($ZrO_2$) of mainly monoclinic crystalline form, depending upon the specific conditions of oxygen and water vapor levels during the process. If the oxidation process is continued to excess, the coating will whiten and tend to separate from the metal underlying metal. An in situ oxidation step may be conducted in either oxygen, air, steam, hot water, salt baths or fluidized beds. For convenience, the metal implant component may be placed in a furnace having an oxygen-containing atmosphere (such as air) and typically heated at 700°–1100° F. for up to about 6 hours. However, other combinations of temperature and time are possible. When higher temperatures are employed, the oxidation time should be reduced to avoid the formation of a less-adherent oxide.

It is preferred that a blue-black zirconium oxide layer ranging in thickness from less than about one micron to about 6 microns should be formed, although thicker coatings of up to about 20 microns are also satisfactory. Furnace air oxidation at 1000° F. for 3 hours will form an oxide coating of about 3–4 microns thickness on (ZIRCADYNE 705). Longer oxidation times and higher oxidation temperatures will increase this thickness, but may compromise coating integrity if the thickness exceeds about 20 microns. For example, one hour oxidation at 1300° F. will form an oxide coating of about 14 microns in thickness, while 21 hours at 1000° F. will form an oxide coating thickness of about 7 to about 9 microns. Of course, because only a thin oxide coating is necessary on the surface, only very small dimensional changes, typically less than 10 microns over the thickness of the prosthesis, will result. In general, thinner coatings (up to about 6 microns) have better attachment strength and more favorable residual surface stresses.

One of the salt-bath methods that can be used to apply the zirconium oxide coatings to the metal alloy prosthesis is described in U.S. Pat. No. 4,671,824 to Haygarth, the teachings of which are incorporated by reference as though fully set forth. The salt-bath method provides a similar, slightly more abrasion resistant blue to black zirconium coating. This method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the method of the Haygarth patent prefers the range 550°–800° C. (1022° F.–1470° F.). However, the lower oxygen levels in the bath produce thinner coatings than the furnace air oxidation at a given time and temperature. A salt bath treatment at 1290° F. for 4 hours produces an oxide coating thickness of roughly 7 microns. Residual contaminants in the salt bath can be inadvertently left on the treated implant surface and produce adverse clinical results. While some of these can be removed by polishing and washing, it is nonetheless preferred to use the gas (air) oxidation or nitridation process which provides less possibility of contamination.

Whether air oxidation in a furnace, in a fluidized bed, or salt bath oxidation is used, the hardness of the zirconium oxide coatings are generally the same. For example, if the surface of a wrought (ZIRCADYNE 705) (Zr, 2–3 wt. % Nb) implant component is oxidized, the hardness of the surface after oxidation is dramatically increased over the 200 Knoop hardness of the original metal surface. The surface hardness of the blue-black zirconium oxide surface following oxidation by either the salt bath or air oxidation process is approximately 1700–2000 Knoop.

In situ air or oxygen oxidation is the preferred method for producing the inventive oxide coatings because it minimizes the potential for surface contamination. Oxygen diffuses into the metal component thereby allowing the formation of a tightly adherent oxide coating while strengthening the underlying zirconium or zirconium alloy metal.

While the above discussion has dealt mainly with blue to black zirconium oxide coatings on prostheses, zirconium nitride (yellow-orange) coatings are also effective in reducing wear on opposing surfaces and preventing corrosion of the underlying metallic composition by body fluids.

Even though air contains about four times as much nitrogen as oxygen, when zirconium or zirconium alloy is heated in air as described above, the oxide coating is formed in thermodynamic preference to the nitride coating. This is because the thermodynamic equilibrium favors oxidation over nitridation under these conditions. Thus, to form an in situ nitride coating the equilibrium must be forced into favoring the nitride reaction. This is readily achieved by eliminating oxygen and using a nitrogen or ammonia atmosphere instead of air or oxygen when a gaseous environment (analogous to "air oxidation") is used.

In order to produce an in situ zirconium nitride coating of about 5 microns in thickness, the zirconium or zirconium alloy annuloplasty ring component should be heated to about 800° C. for about one hour in a nitrogen atmosphere. Thus, apart from the removal of oxygen (or the appropriate reduction in oxygen partial pressure) or increasing the temperature, conditions for forming the zirconium nitride coating do not differ significantly from those needed to form the blue to black zirconium oxide coating. Any necessary adjustment would be readily apparent to one of ordinary skill in the art.

When a salt bath method is used to produce an in situ nitride coating, the oxygen-donor salts should be replaced with nitrogen-donor salts, for instance, cyanide salts. Upon such replacement, a nitride coating can be obtained under similar conditions to those needed for obtaining an oxide coating. Such modifications as are necessary can be readily determined by those of ordinary skill in the art.

Alternatively, the zirconium oxide or nitride can be deposited onto the zirconium or zirconium alloy surface via methods other than the in situ gaseous and salt bath processes described above. These methods encompass, for example, standard physical or chemical vapor deposition, including those using an ion-assisted deposition.

As in the case of the zirconium oxide coatings, the nitride coatings are useful even at thicknesses as low as about 0.1 micron. However, thicknesses from about 1 to about 20 microns are preferred and the range about 3 to about 6 microns is most preferred.

If desirable for a particular application, the zirconium oxide or nitride coated component can be further coated by silver doping or boronation so as to improve wear-resistance. Additionally, amorphous diamond-like carbon, or other hard, biocompatible coatings can also be applied to either the low modulus component metal or to the oxidized or nitrided surface layer. When deposited over the hard oxide or nitride surface layer, amorphous diamond-like carbon and other types of hard overlay coatings will have improved attachment strength due to their closer hardness match with the surface layer than the match between such overlay coatings and relatively softer component metal surfaces.

Further details regarding the characteristics, properties, production, and benefits of zirconium oxide and zirconium nitride coatings, as well as the additional coatings discussed above, are described in U.S. Pat. No. 5,496,359, U.S. Pat. No. 5,282,022, U.S. Pat. No. 5,282,850, U.S. Pat. No. 5,152,794, and U.S. Pat. No. 5,037,438, all of which are hereby fully incorporated by reference.

Figure 2:
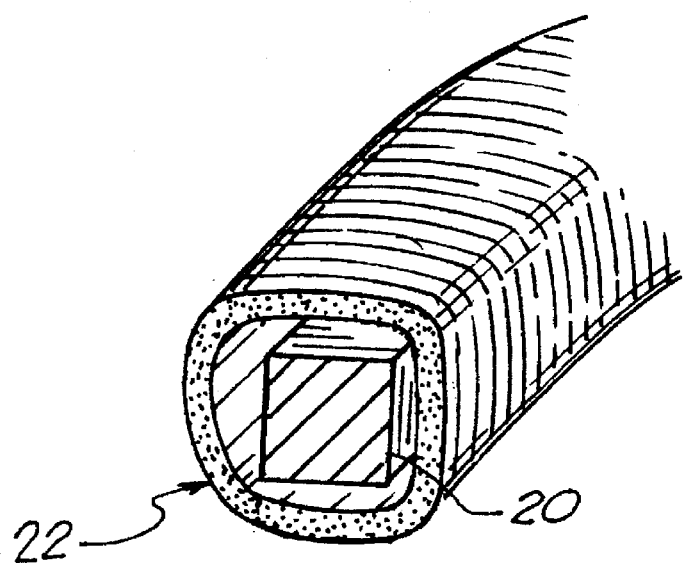
FIG. 2 is a cross-sectional diagram of the ring in FIG. 1 along the plane A—A.

FIG. 1 shows a valvular annuloplasty ring construct 10. Valvular annuloplasty ring construct 10 is shown in cross-section in FIG. 2 and includes an inner core component 20 and an encasing woven sleeve component 22. An inventive annuloplasty ring embodiment of this type of construction would have the core 20 at least partially fabricated of a low elastic modulus metallic composition with a coating of zirconium oxide ranging in color from blue to black.

In another preferred embodiment of the inventive annuloplasty ring, the core 20 is encased in sleeve 22 woven from wire fabricated of a low elastic modulus metallic composition with a coating of zirconium oxide ranging in color from blue to black.

Figure 3:
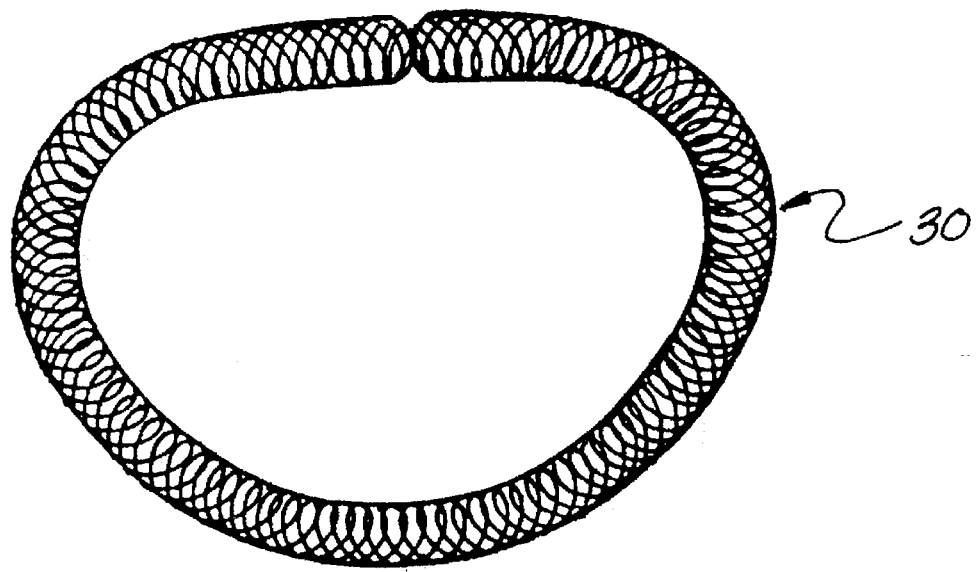
FIG. 3 is a schematic representation of a tricuspid annuloplasty ring sold under the trademark (CARPENTIER-EDWARDS) by Baxter Healthcare.
Figure 4:
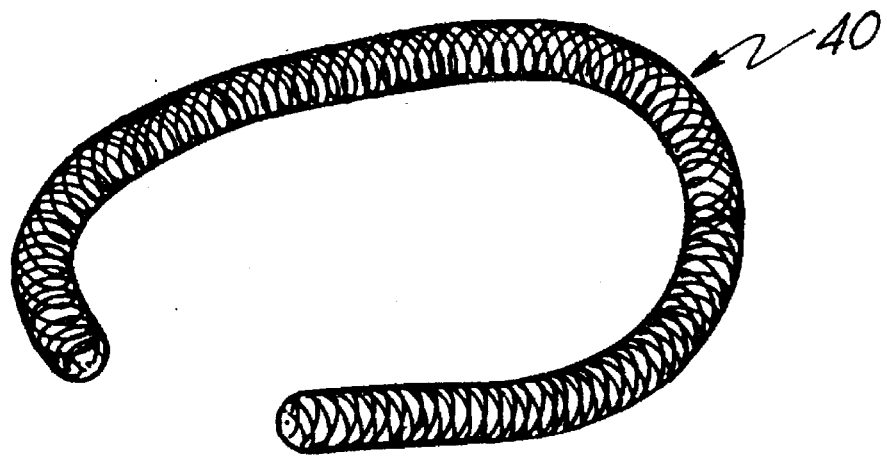
FIG. 4 is a schematic representation of a mitral annuloplasty ring sold under the trademark (CARPENTIER-EDWARDS) by Baxter Healthcare.
Figure 5:
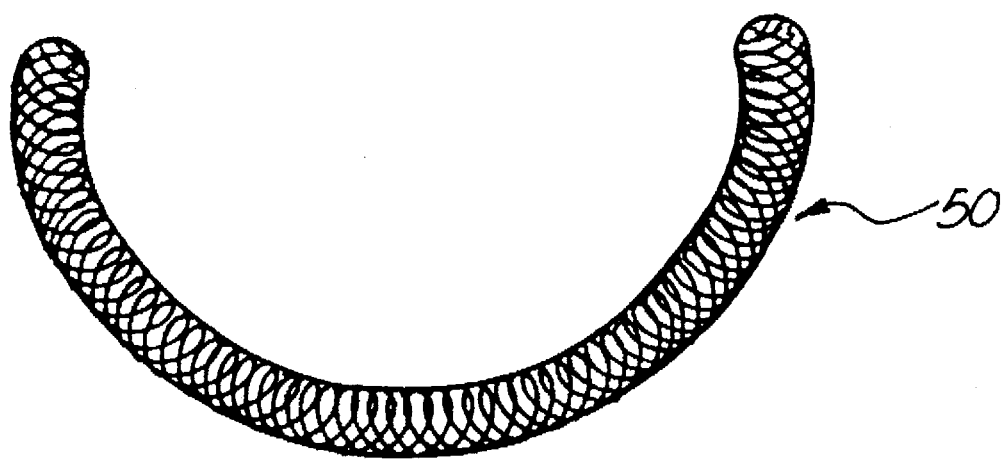
FIG. 5 is a schematic representation of another annuloplasty ring sold under the trademark (COSGROVE EDWARDS) by Baxter Healthcare.

FIG. 3 shows a tricuspid annuloplasty ring construct 30, FIG. 4 a mitral valve ring construct 40, and FIG. 5 yet another annuloplasty ring construct 50.

The invention is, of course, not limited in its application to the annuloplasty constructs of FIGS. 1–5 but includes all suitable annuloplasty rings.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. An annuloplasty ring for implantation in living body tissue of a patient, the annuloplasty ring having enhanced resistance to wear, comprising:
   (a) at least one component fabricated from a low elastic modulus metallic composition, the elastic modulus being less than about 130 GPa and the component having outer surfaces; and
   (b) a corrosion-resistant, biocompatible, hemocompatible, hard, durable, stable coating at least partially covering the outer surfaces of said component, said coating selected from the group consisting essentially of zirconium oxides, ranging in color from blue to black, and zirconium nitrides, ranging in color from yellow to orange.

2. The annuloplasty ring of claim 1, wherein said coating is up to about 20 microns in thickness.

3. The annuloplasty ring of claim 1, wherein said low elastic modulus metallic composition includes a metal selected from the group consisting of zirconium and zirconium-containing alloys.

4. The annuloplasty ring of claim 3, wherein the component further includes a sub-surface zone containing diffused oxygen.

5. The annuloplasty ring of claim 3 or claim 4, wherein said coating includes diffusion-bonded zirconium oxides.

6. The annuloplasty ring of claim 5, wherein said coating is up to about 20 microns in thickness.

7. The annuloplasty ring of claim 1, further including a second coating selected from the group consisting of antibiotics, anticoagulants and platelet adhesion reducers, wherein said second coating is disposed on said corrosion-resistant, biocompatible, hemocompatible, hard, durable, stable coating.

8. The annuloplasty ring of claim 7, wherein said platelet adhesion reducer is phosphatidyl choline.

9. The annuloplasty ring of claim 7, wherein said platelet adhesion reducer is heparin.

10. The annuloplasty ring of claim 1, further including a silver-doped overlay coating over said corrosion-resistant, biocompatible, hemocompatible, hard, durable, stable coating.

11. The annuloplasty ring of claim 1, further including a hard overlay coating over said coating, said hard overlay coating selected from the group consisting of amorphous diamond-like carbon, cubic zirconia, and white tetragonal zirconia.

12. The annuloplasty ring of claim 1, wherein said components include a core and a woven sleeve.

13. The annuloplasty ring of claim 1, further including a lubricious boron-containing overlay coating over said corrosion-resistant, biocompatible, hemocompatible, hard, durable, stable coating.

* * * * *